United States Patent
Presant et al.

(10) Patent No.: US 6,274,115 B1
(45) Date of Patent: *Aug. 14, 2001

(54) METHOD OF TARGETING A SPECIFIC LOCATION IN A BODY USING PHOSPHOLIPID AND CHOLESTEROL LIPOSOMES WHICH ENCAPSULATE AN AGENT

(75) Inventors: Cary A. Presant, San Marino; Richard T. Proffitt, Arcadia; Raymond L. Teplitz, Pasadena; Lawrence E. Williams, San Dimas; George W. Tin, Arcadia, all of CA (US)

(73) Assignee: Gilead Sciences, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/483,494

(22) Filed: Jun. 7, 1995

Related U.S. Application Data

(63) Continuation of application No. 06/663,503, filed on Oct. 22, 1984, now Pat. No. 5,435,989, which is a continuation-in-part of application No. 06/363,593, filed on Mar. 30, 1982, now abandoned.

(51) Int. Cl.[7] .......................... A61K 51/00; A61K 9/127
(52) U.S. Cl. ........................................... 424/1.21; 424/450
(58) Field of Search ................... 424/1.21, 1.11, 424/450, 1.45; 436/829; 600/3

(56) References Cited

U.S. PATENT DOCUMENTS

| | | |
|---|---|---|
| 3,932,657 | 1/1976 | Rahman et al. . |
| 3,957,971 | 5/1976 | Oleniacz et al. . |
| 3,992,513 | 11/1976 | Petkau et al. . |
| 3,993,754 | 11/1976 | Rahman et al. . |
| 4,016,290 | 4/1977 | Rahman et al. . |
| 4,186,183 | 1/1980 | Steck et al. . |
| 4,193,983 | 3/1980 | Ullman et al. . |
| 4,224,179 | 9/1980 | Schneider, et al. . |
| 4,235,871 | 11/1980 | Papahadjopoulos et al. . |
| 4,241,046 | 12/1980 | Papahadjopoulos et al. . |
| 4,298,594 * | 11/1981 | Sears et al. ............. 424/450 |
| 4,310,505 | 1/1982 | Baldeschwieler et al. . |
| 4,310,506 | 1/1982 | Baldeschwieler et al. . |
| 4,377,567 | 3/1983 | Geho et al. . |
| 4,497,791 | 2/1985 | Gamble et al. . |
| 4,544,545 | 10/1985 | Ryan et al. . |
| 4,755,388 | 7/1988 | Heath et al. . |
| 4,769,250 | 9/1988 | Forssen et al. . |
| 4,865,835 | 9/1989 | Begent et al. . |
| 4,925,661 | 5/1990 | Huang et al. . |
| 5,019,369 | 5/1991 | Presant et al. . |
| 5,435,989 | 7/1995 | Presant et al. . |
| 5,441,745 | 8/1995 | Presant et al. . |

FOREIGN PATENT DOCUMENTS

2249552 U  10/1972  (DE) .

OTHER PUBLICATIONS

Espinola, L.G. (1979) *J. Nucl.Med.*, vol. 20(5), 434–40, No month provided.

Gregoriadis, et al (1980) Chemical Abstracts, vol. 93, No. 26, p.382, Abstract No. 245393d, "The Phospholipid Component of Small Unilamellar Liposomes Controls the Rate of Clearance of Entrapped Solutes from the Circulation" Febs.Lett. 1980, 119(1), 43–6, No month provided.

Hwang, et al (1977), *Proc.Nat.Acad.Sci.*, vol. 11, 4991–95. No month provided.

Machy, P., et al (1983) Chemical Abstracts, vol. 99, No. 6, 307–07, Abstract No. 433935. No month provided.

Machy, P., et al (1983) "Small Liposomes are Better than Large Liposomes for Specific Drug Delivery in Vitro"Biochim.Biophys.Acta. 730:313–20. No month provided.

Mauk, et al (1974) *Proc. Natl.Acad.Sci.USA*, 76(2), pp. 765–769. No month provided.

Mauk, et al (1980) Science 207:309–11. No month provided.

Proffitt, et al (1983) Science 220(2):502–04. No month provided.

Proffitt, et al (1983) *J. Nucl.Med.*, 24(1), p.45–51. No month provided.

Proffitt, et al (1981) *Proc. Amer. Assn. Cancer Research*, Abstract #162. No month provided.

Richardson, et al (1979), Brit. J. Cancer, 40, 35–43. W/o month.

Richardson, et al (1978), *J.Nucl. Med.*, 19(9), p. 1049–54. W/o month.

Ryman, et al (1983), *Biol. Cell*, 47:71–80. W/o month.

White, et al (1983) Chemical Abstracts, vol. 99, p.314, Abstract No. 43459t. W/o month.

White, et al (1983) Cholesterol on the Stability of Liposomes Containing Methotrexate, Biochem.Soc. Trnas. 11(3):305–06. W/o month.

Wu, et al (1981), *Biochemistry*, 78:2033–2037. No month provided.

Yatvin, et al (1982) Med. Phys. 9:149–175. No month provided.

Anighileri et al (1976) J. Nucl. Biol. Med., 20, 165–67. No month provided.

(List continued on next page.)

Primary Examiner—Michael G. Hartley
(74) Attorney, Agent, or Firm—Mark L. Bosse

(57) ABSTRACT

Micellular particles such as small unilamellar vesicles of less than 2000 A° loaded with $^{111}$In are administered to BALB/c mice in which EMT6 tumors had been induced. Whole body scintographs of the mice to which either neutral or positively or negatively charged vesicles had been administered show a substantial quantity of the vesicle entrapped $^{111}$In localized in the tumor. Blocking of macrophages in the liver and spleen by first administering unlabeled, aminomannose substituted vesicles before administration of the labeled vesicles increases uptake of the $^{111}$In labeled vesicles in the tumor.

1 Claim, 3 Drawing Sheets

OTHER PUBLICATIONS

Chawla, et al (1980) Chemical Abstracts, vol. 92, p.339, Abstract No. 169129, "The Effect of Liposomal Change on Drug Toxicity and Efflux" *J.Pharm.Pharmacol*, 1979 31 Supp. (Br.Pharm.Conf. 1979). No month provided.
DeBarsy et al (1976) *Laboratory Investigation*. vol. 34(3), 273–82. No month provided.
Allen et al.(1983) J. Pharmacol Exp. Ther. 226:539.
D. Silva et al.(1982) J. Pharm. Sci. 71:1394.
Forssen et al.(1979) Biochem. Biophys. Res. Commun. 91:1295.
Forssen et al.(1981) Proc. Natl. Acad. Sci. USA 78:1873.
Forssen et al.(1983) Cancer Res. 43:546.
Freise et al.(1982) Arch. Int. Pharmacodyn Ther. 258:180.
Ganapathi et al.(1980) Cancer Res. 40:630.
Goodwin et al.(1972) Radiology 105:699.
Juliano et al.(1978) Biochem. Pharmacol 27:21.
Kirby et al.(1980) Biochem. J. 186:591.
Kirby et al.(1983) Biochem. Pharmacol 32:609.
Meares et al.(1969) Proc. Natl. Acad. Sci. USA 64:1155.
Meares et al.(1972) Proc. Natl. Acad. Sci. USA 69:3718.
Rahman et al.(1980) Cancer Res. 40:1532.
Rustum et al.(1979) Cancer Res. 39:1390.
van Hoesel et al.(1984) Cancer Res. 44:3698.
Williams et al.(1984) J. Nucl. Med. Allied Sci. 28:35.
Dapergolas et al. (1976) FEBS Letters 63:235.
Deliconstantinos et al. (1977) Biochem. Soc. Trans. 5:1326.
Gregoriadis et al. (1977) Life Sciences 21:357.
Gregoriadis et al. (1971) FEBS Letters 14:95.
Gregoriadis (1973) FEBS Letters 36:292.
Gregoriadis (1972) Biochem. J. 129:123.
Gregoriadis (1974) Eur. J. Biochem. 47:179.
Kimmelberg et al. (1975) Life Sciences 17:715.
Kosloski et al. (1978) Cancer Research 38:2848.
Mayhew et al. (1976) Cancer Research 36:4406.
Neerunjun et al. (1977) Biochem. Soc. Trans. 5:1380.
Richardson et al. (1977) Biochem Soc. Trans. 5:290.
Hashimoto et al. (1983) Cancer Research 43:5328.
Forssen et al . (1983) Cancer Treatment Rpts. 67:481.
Gabizon et al. (1982) Cancer Res. 42:4734.
Gabizon et al. (1983) Cancer Res. 43:4730.
Poste (1983) Biol. Cell 47:19.

* cited by examiner

| Tissue | % injected dose per per gram of tissue* |
|---|---|
| Blood | 1.1 ± 0.2 |
| Tibias | 5.5 ± 0.5 |
| Lung | 3.7 ± 0.8 |
| Liver | 50.7 ± 2.1 |
| S & L Intestine# | 0.9 ± 0.0 |
| Kidney | 5.9 ± 0.3 |
| Spleen | 73.2 ± 13.9 |
| Carcass | 0.9 ± 0.1 |
| Stomach# | 0.2 ± 0.0 |
| Muscle | 0.3 ± 0.0 |
| Skin | 0.8 ± 0.0 |
| S.C. LLC Tumor | 2.1 ± 0.1 |
| Granuloma | 0.6 ± 0.1 |
| % of Recovery | 81.8 ± 0.9 |
| Tumor Mass (mg) | 4 ± 1 |

*Mean values ± standard error of the mean
N = number of mice per group
values include organ contents

FIG. 1

24 h % Injected Dose Per Gram of Tissue*

Number of days after subcutaneous
implantation of Lewis Lung Carcinoma

| Tissue | 8<br>N=4+ | 11<br>N=4+ | 17<br>N=4+ |
|---|---|---|---|
| Blood | 8.1 ± 0.01 | 11.4 ± 2.3 | 1.3 ± 0.4 |
| Tibias | 6.4 ± 0.6 | 6.8 ± 0.6 | 4.7 ± 0.7 |
| Lung | 5.7 ± 0.5 | 15.1 ± 1.4 | 12.6 ± 1.6 |
| Liver | 50.0 ± 2.4 | 50.5 ± 1.9 | 36.1 ± 3.2 |
| S & L Intestine# | 4.3 ± 0.2 | 4.9 ± 0.6 | 1.8 ± 0.3 |
| Kidney | 15.1 ± 0.5 | 15.8 ± 0.4 | 9.2 ± 0.2 |
| Spleen | 57.0 ± 5.6 | 50.0 ± 6.7 | 22.2 ± 3.2 |
| Carcass | 2.3 ± 0.1 | 2.8 ± 0.2 | 1.6 ± 0.1 |
| Stomach* | 3.5 ± 0.6 | 4.3 ± 1.3 | 1.5 ± 0.5 |
| Muscle | 1.1 ± 0.1 | 0.8 ± 0.0 | 0.4 ± 0.0 |
| Skin | 5.6 ± 2.7 | 2.1 ± 0.3 | 2.4 ± 0.2 |
| S.C. LLC Tumor | 23.7 ± 2.7 | 17.0 ± 3.3 | 9.8 ± 0.9 |
| % of Recovery | 102.8 ± 0.6 | 105.0 ± 1.9 | 91.3 ± 1.5 |
| Tumor Mass (g) | 0.13 ± 0.04 | 0.16 ± 0.04 | 1.67 ± 0.39 |

*Mean values ± standard error of the mean
N = number of mice per group
values include organ contents

FIG.2

| TISSUE | DS PC:Ch:AM (8:3:1) (AM/2) BLOCKADE | In ¹¹¹In-NTA DS PC:Ch (2:1) | In ¹¹¹In-NTA DS PC:Ch:SA (4:1:1) | In ¹¹¹In-NTA DS PC:Ch:DP (4:1:1) |
|---|---|---|---|---|
| TUMOR | + | 26.4 | 11.8 | 11.7 |
|  | - | 18.5 | 6.1 | 11.9 |
| LIVER | + | 10.2 | 17.6 | 17.3 |
|  | - | 14.6 | 28.5 | 16.6 |
| SPLEEN | + | 10.5 | 32.4 | 32.7 |
|  | - | 18.8 | 43.8 | 39.3 |
| LUNG | + | 8.0 | 2.8 | 3.8 |
|  | - | 6.0 | 1.8 | 3.0 |
| KIDNEY | + | 6.6 | 7.8 | 17.8 |
|  | - | 6.8 | 6.8 | 17.1 |
| BLOOD | + | 7.9 | 2.4 | 1.7 |
|  | - | 6.6 | 1.0 | 1.3 |

FIG.3

| TREATMENT | [³H] MTX IN TUMOR (dpm/gm) | TREATMENT CONTROL | [¹⁴C] LIPID IN TUMOR (dpm/gm) |
|---|---|---|---|
| FREE [³H] MTX | 6,700 | 1.0 | — |
| LIPOSOME ENTRAPPED [³H] MTX | 20,150 | 3.0 | 12,570 |
| LIPOSOME ENTRAPPED [³H] MTX; AFTER AM/2 BLOCKADE | 19,000 | 2.8 | 12,670 |

FIG.4

METHOD OF TARGETING A SPECIFIC LOCATION IN A BODY USING PHOSPHOLIPID AND CHOLESTEROL LIPOSOMES WHICH ENCAPSULATE AN AGENT

RELATIONSHIP TO OTHER APPLICATIONS

This is a continuation of application Ser. No. 06/663,503, filed Oct. 22, 1984, U.S. Pat. No. 5,435,989; which is a continuation-in-part of application Ser. No. 06/363,593, filed Mar. 30, 1982, now abandoned.

FIELD OF THE INVENTION

This invention relates to a method of targeting specific locations as, for example, tumors, in a body, by use of micellular particles such as phospholipid vesicles. The invention may be used for diagnosis and/or treatment of such abnormalities.

DESCRIPTION OF PRIOR ART

Before various abnormalities in a patient's body can be diagnosed and treated, it is often necessary to locate the abnormalities. This is particularly true of abnormalities such as malignant tumors since the treatment of such tumors is often on a localized basis. For example, the location of cancer cells has to be identified so that a therapeutic agent can be directed to such cells to eliminate the tumor.

Various attempts have been made over an extended number of years to identify specific locations, such as tumors, in a patient's body by simple techniques. For example, it would be desirable to identify the location of cancer cells by a simple method involving the introduction of a particular chemical to the patient's body and the movement of such chemical to such specific locations. It would also be desirable to treat the cancer by introducing modified chemicals into the patient's body and having such chemicals move to specific locations to combat the cancer cells at such locations. In spite of such attempts, however, simple delivery systems for targeting specific locations, such as tumors, for treatment or diagnosis do not exist as yet.

Placing a chemotherapeutic drug in the body orally, subcutaneously or intravenously can result in harm to the normal cells in the body which take up the drug and a worsening in the patient's condition, without achieving the desired reduction in tumor cell activity. In the past, this toxicity to normal cells in the patient's body has been a major disadvantage in the treatment of tumors with chemotherapeutic agents. The lack of efficacy of such chemotherapy is also attributable to the failure of the freely circulating drug to localize within tumor cells before it is excreted or taken up by other cells in the body.

Prior attempts to improve treatment of tumors by chemotherapeutic agents have included encapsulation of such agents within biodegradable phospholipid micellular particles in the form of vesicles or liposomes. Encapsulation is thought to reduce the potential toxicity from the circulating drugs. Researchers have also sought to utilize such encapsulation to selectively target tumors within a body for delivery of chemotherapeutics. However, until the invention disclosed in the present application and the related application Ser. No. 363,593, efforts to locate or treat tumor cells with drug-encapsulating targeting particles have not been successful.

The inability to provide a satisfactory targeting method is believed to be due to the nature of the solid tumors and their metastases which are located in extravascular tissues. Thus, to accomplish targeting of intravenously injected radiolabelled or chemotherapeutic agents to the tumor cells, the agents must leave the normal circulation by crossing the blood vessel membranes to enter the extravascular tissues. This movement is known as "extravasation". In addition the encapsulated agent must cross the tumor cell membrane. Normally, small substances such as small molecular weight proteins and membrane-soluble molecules can cross cell membranes by a process known as passive diffusion. However, passive diffusion will not allow sufficient accumulation of larger particles carrying drugs within cells to reach therapeutic levels. Additionally, cells can actively transport materials across the membrane by a process such as pinocytosis wherein extracellular particles are engulfed by the membrane and released inside the cell. Entry of encapsulating particles into individual cells may occur by pinocytosis.

Progress in targeting such specific locations with chemotherapeutic drugs has been hampered by the inability to accomplish and detect movement of drug carriers across blood vessel membranes. In the usual case, large structures such as drug encapsulating vesicles cannot escape from blood vessels such as capillaries, and thus remain in circulation.

An understanding of extravasation, however, requires an examination of the structure of the vascular morphology of a tumor. Various blood vessels are associated with tumors, in particular capillaries. It is now known that tumor capillaries may exhibit alterations in their structure, such as fenestrations, as a result of tumor cell growth patterns. H. I. Peterson, *Vascular and Extravascular Spaces in Tumors: Tumor Vascular Permeability,* Chapter III, Tumor Blood Circulation, H. I. Peterson, Ed. (1979). Studies of tumor capillary permeability reveal morphologic variations in the capillaries which allow some substances to cross the capillary membrane. Such variations include defects in vascular endothelium from poor cell differentiation, or breaks in vascular walls as a result of invading tumor cells. H. I. Peterson, supra.

Notwithstanding such knowledge of tumor vascular morphology, researchers such as Peterson have concluded that transport of large molecules or materials across the tumor capillary wall occurs as a result of passive diffusion and that "concentrations of active drugs sufficient for therapeutic effect are difficult to reach." H. I. Peterson, supra, at 83.

Prior to such morphologic studies, early reports suggested that vesicles might undergo transcapillary passage across the capillary membranes into tumor cells. G. Gregoriadis, *Liposomes in Biological Systems,* Gregoriadis, Ed., Ch 2, (1980). However, available data indicated that the vesicles were unstable in vivo and that the radiolabel may have leaked, thus apparently prompting alternative theories such as longer circulation of vesicles in the blood with release of drugs at a slower rate and interaction of the liposomes with the capillary walls without crossing the wall surface, which presumably resulted in the drugs within tumors. Id. Other researchers simply have concluded that the vesicles do not penetrate vascular walls after intravenous administration. B. Ryman et al., *Biol. Cell,* Vol 47, pp. 71–80 (1983); G. Poste, *Biol. Cell,* Vol. 47, pp. 19–38 (1983).

Thus, although the prior art has recognized that vesicles carrying therapeutic drugs must cross vascular barriers to reach tumor cells, the experience of the art has taught that intravenous administration is not effective to deliver encapsulated drugs to extravascular tumor cells. This invention accordingly provides simple methods of enhancing extravasation of encapsulated chemotherapeutic agents to tumor cells within a body. The method of this invention further provides for the identification of such tumor sites in the body.

SUMMARY OF THE INVENTION

The method of this invention includes the provision of phospholipid micellular particles such as vesicles. Pure (more than approximately 98% pure), neutral phospholipid molecules are incorporated into small (less than 2000A°) micelles so that they are a component of the external surface. The phospholipid molecules and/or vesicle contents may be radiolabeled to enhance the identity of the specific location and the diagnosis of the tumor at the specific location.

The phospholipid molecules may constitute distearoyl phosphatidylcholine. The stability of the distearoyl phosphatidylcholine micelles may be enhanced by the incorporation of cholesterol. Positively charged molecules such as stearylamine or aminomannose or aminomannitol derivatives of cholesterol or negatively charged molecules such as dicetyl phosphate may also be incorporated into the vesicles.

When phospholipid micelles are introduced into the blood stream of a patient, the micelles move to the specific locations of cancerous growth in the patient's body, which may then be identified and treated. Drugs may be included in phospholipid vesicles and such drug-bearing vesicles may then be introduced into the patient's body for targeting the tumor locations.

To enhance movement of the phospholipid vesicles to the specific locations, positively charged phospholipid vesicles may first be introduced into the patient's blood stream to block the macrophages in the patient's body. The positively charged molecules bound to such phospholipid vesicles may be an aminomannose or aminomannitol derivative of cholesterol. Concurrently or after a suitable period of time such as approximately one (1) hour, other phospholipid vesicles may be introduced into the patient's blood stream to move to the specific locations in the body. Such phospholipid vesicles may include cholesterol and may be neutral or may be positively charged as by the inclusion of a stearylamine or aminomannose or aminomannitol derivative of cholesterol or may be negatively charged as by the inclusion of a dicetyl phosphate.

When the phospholipid vesicles are introduced into the body to target tumors, indium-111 may be used as the labelling agent. The indium-111 may be chelated to a suitable material such as nitrilotriacetic acid (NTA). NTA is advantageous because it forms a weak bond with the indium-111. As a result, when the phospholipid vesicles reach the tumor, the nitrilotriacetic acid is displaced by proteins at the tumor. Since the proteins have a strong bond with the indium-111, the indium-111 remains at the tumor for a long period of time (in excess of 24 hours), which provides for easy identification of the tumor over the extended period of time.

BRIEF DESCRIPTION OF THE DRAWINGS

FIG. 1 is a table illustrating the targeting of phospholipid vesicles to tumors in a body;

FIG. 2 is a table illustrating the targeting and blocking of macrophages in the liver and spleen by phospholipid vesicles;

FIG. 3 is a table illustrating the targeting of phospholipid vesicles to tumors in the body after the blocking of the macrophages in the liver and spleen; and FIG. 4 is a table illustrating the enhanced delivery of drugs to a tumor in a body by the use of phospholipid vesicles.

DETAILED DESCRIPTION OF THE INVENTION

As used herein, "micellular particle" and "micelles" refer to particles which result from aggregations of amphiphilic molecules. In this invention preferred amphiphiles are biological lipids. Micelles are water-soluble aggregates of molecules with hydrophobic and hydrophilic portions (so-called amphiphilic molecules) which associate spontaneously. Such micelles can be in the form of small spheres, ellipsoids or long cylinders, and can also consist of bilayers with two parallel layers of amphiphilic molecules. Such bilayered micelles usually take the shape of spherical vesicles with an internal aqueous compartment. Useful compositions of these micelles include phospholipid molecules in the structure.

"Vesicle" refers to a micelle which is in a generally spherical form, often obtained from a lipid which forms a bilayered membrane and is referred to as a "liposome". Methods for forming these vesicles are, by now, well known in the art. Typically, they are prepared from a phospholipid, for example, distearoyl phosphatidylcholine, and may include other materials such as neutral lipids, for example, cholesterol, and also surface modifiers such as positively or negatively charged compounds.

Materials and Methods

Liposome Preparation. Small unilamellar vesicles (SUV) with the ionophore A23187 were prepared distearoyl phosphatidylcholine (DSPC), cholesterol (Ch), dicetyl phosphate (DP), stearylamine (SA) and the 6-aminomannose (AM), and 6-aminomannitol (AML) derivatives of cholesterol, according to previous methods. Briefly, chloroform solutions of 10 mg lipid with the following molar ratios: DSPC:Ch, 2:1; DSPC:Ch:X, 4:1:1 where X=SA, DC or AML; and DSPC:Ch:AM, 8:3:1, were evaporated to dryness under nitrogen ($N_2$) and further dried under vacuum overnight. Each tube was filled with 0.6 ml phosphate 10 mM phosphate buffered 0.9 saline, pH 7.4 (PBS), containing 1 mM nitrilotriacetic acid (NTA) and sonicated under $N_2$, for 5 to 15 minutes with a MSE sonicator equipped with a titanium microtip.

Liposomes were annealed at 60° C. for 10 minutes and centrifuged at 300× g. Liposomes were separated from unencapsulated NTA with a 30×1.5 cm Sephadex G-50 column. Liposome size was determined by electron microscopy of preparations negatively stained with uranyl acetate. All vesicle types were shown by electron microscopy to have a mean diameter less than 0.1 microns (1000A°). For example, DSPC:Ch vesicles had a mean diameter of approximately 528A°. However, vesicles as large as approximately 2000 Angstroms are believed to be satisfactory in obtaining the desired results of this invention, although the preferred range is approximately 500 to about 700 A°.

The vesicles obtained as described above are chemically pure. By "chemically pure" is meant that the materials which constitute phospholipid vesicles are more than 98% pure. For example, when the phospholipid chemical added is distearoyl phosphatidylcholine, this material is used at more than 98% purity. The same constraint holds for other components, such as cholesterol, which compose the vesicle. The phospholipid vesicles obtained as described above are stable when injected into experimental animals.

The aminomannose and aminomannitol derivatives of cholesterol extend externally from the phospholipid particles. Thus, when such derivatives are incorporated or associated into the surfaces of vesicles or other micelles, an amine moiety is provided that extends approximately 5–15 Angstroms, preferably about 10 Angstroms, beyond the surface of the micelles. In the case of vesicles, it appears that the appropriate molecular design comprises a hydrophobic portion which serves to anchor the molecule within the vesicular bilayer, and a linking portion which is at least mildly hydrophilic which spans the requisite distance between the hydrophobic region and the amino functional group. The hydrophilicity is apparently required to prevent the link from internalizing within the bilayer also and thus serves to "extend" the amine from the surface. An example of a successful extended amine within the context of this invention is a 6-aminomannose cholesterol derivative such as, for example, 6-(5-cholesten-3β-yloxy)hexyl-6-amino-6-deoxyl-thio-D-mannopyranoside. In this example, the cholesterol portion provides the hydrophobic moiety, while the aminomannose is relatively hydrophilic. Other embodiments are also possible: other amino sugars attached to other cholesterol derivatives, for example, are equally suitable as alternative embodiments of the hydrophilic and hydrophobic portions. Polyamines and polyamino acids which can be bound covalently or associated by other means to the vesicle or other micelle surface may also be used.

The amino derivatives and cholesterol tend to impart stability to the phospholipid vesicles. Cholesterol may be included in the range of approximately 0% to 50% of cholesterol by weight and the remainder constituting the phospholipids. The charged molecules such as the stearylamine, the dicetyl phosphate and the aminomannose and aminomannitol derivatives of cholesterol may be included in the range of 0% to 20% by weight of the charged molecules and the remainder constituting the phospholipids.

The chemically pure liposome compositions discussed above are quite stable to leakage in vitro and in vivo. However, phospholipid mixtures such as egg lecithin form more fluid membranes than pure phospholipids. As a result, liposomes from natural lecithin mixtures are less stable to leakage of their contents than pure phospholipids.

In-111 Loading Procedure. Loading of In-111 into preformed liposomes was facilitated by the presence of A23187 in the lipid bilayer. In-111 was loaded into liposomes at 60–80° C. as previously described. Incubations were terminated by the addition of 10 mM ethylenediaminetetraacetic acid (EDTA) in 10 mM phosphate buffered 0.9% sodium chloride, pH 7.4 (PBS), and free In-111 was separated from the loaded liposomes by chromatography on Sephadex G-50. Up to 90% of the added In-111 could be incorporated into preformed liposomes by this technique, and specific activities of up to 300 $\mu$Ci/mg lipid have been obtained.

EMT6 Tumor Growth. Male BALB/c mice weighing 20–25 g were injected subcutaneously on the right hind leg with 5×10 EMT6 cells in 0.1 ml sterile phosphate buffered saline. Tumors were allowed to grow for 10–20 days prior to using these animals for imaging studies. At this stage, tumors weighed between 0.2 and 0.4 gm. Up to 0.5 ml PBS containing 1 to 2 mg liposomes loaded with up to 30 $\mu$Ci In-111 were injected into the tail vein of each animal. Control animals were injected with In-111-NTA which had not been encapsulated in liposomes.

Gamma Camera Imaging. At one (1) hour and at twenty-four (24) hours after injecting In-111 loaded liposomes, each animal was anesthetized with 40 mg/kg sodium pentobarbital and positioned on a platform 12 cm from the gamma scintillation camera equipped with a 6 mm pinhole. Whole-body dorsal images were acquired on x-ray film and corresponding digitized data were stored on magnetic discs for computer analysis.

Biodistribution of Radioactivity. Immediately after the twenty-four (24) hour images were acquire, animals were sacrificed and dissected to determine the organ distribution of radio-activity. Organs or tissues were excised, washed in PBS, blotted dry, and weighted. Radioactivity was measured in a well-type gamma-ray spectrometer and quantitated based on activity present in liposomes before injection. In some experiments, the gamma-ray perturbed angular correlation technique was used to measure the rotational correlation time of the In-111 in individual tissues and thereby assess the proportion of isotope remaining in intact liposomes.

RESULTS

Whole body scintographs were made of tumor bearing mice which had been injected intravenously with In-111 NTA small phospholipid vesicles SUV 24 hr previously. EMT6 tumor images were clearly discernible in animals injected with neutral, negative and positively charged phospholipid vesicles. A comparison of the biodistribution of In-111 NTA delivery by each of these vesicle types can be made from the data presented in FIG. 1. As will be seen from the second column of FIG. 1, neutral phospholipid vesicles provided the best delivery of In-111 to tumor tissue. The specific targeting of the phospholipid vesicles to the tumors in this instance was at least as high as the targeting of the phospholipid vesicles to the liver or spleen, the usual target tissues of liposomes, and was nearly 8 times greater than the specific activity observed at the tumors when free In-111 NTA was injected in vivo. This will be seen from a comparison of the results shown in the first and second columns to FIG. 1. It can also be seen in FIG. 1 that, as liver and spleen uptake of In-111 decreases, the concentration of the phospholipid vesicles remaining in the blood increases. Also the increase in tumor associated radioactivity correlates approximately with the blood level of In-111.

Applicants have previously demonstrated a strong association with EMT6 tumor cells in vitro of liposomes with 6-aminomannose derivatives of cholesterol. Applicants accordingly attempted tumor imaging with phospholipid vesicles of aminomannose derivatives of cholesterol where such vesicles were labeled with In-111. Applicant's observations in this experiment confirmed that the vast majority of In-111 in such phospholipid vesicles ultimately is deposited in the liver and spleen. Tumor images could not be obtained with such phospholipid vesicles as demonstrated in columns 2 and 3 of FIG. 2 by the low deposition of the phospholipid vesicles in the tumor. The low deposition of the phospholipid vesicles in the tumor may result from the fact that most of such vesicles are taken up by the liver and spleen.

Liposomes with a lower concentration of the 6-AM derivative of cholesterol do not get trapped in the lung, so it seemed reasonable to assume that AM/2 vesicles (third column of FIG. 2) loaded with In-111 might be better tumor imaging agents than the material shown in the second column of FIG. 2. A comparison of the second and third columns of FIG. 2 shows that this was not the case. In fact, the AM/2 vesicles had a very high affinity for the liver and spleen. For example, after a period of 24 hours from the time of injection of the lipid vesicles in the blood stream, the combined radioactivity in the liver and spleen averaged greater than 75% of the total injected dose. This was the highest amount of liver and spleen uptake of vesicles observed of the several lipid composition studies.

Applicants have previously shown that positively charged liposomes were bound to EMT6 cells in vitro to a much greater extent than either neutral or negatively charged liposomes. Applicants accordingly investigated AML derivatives of cholesterol, another synthetic glycolipid derivative with positive charge. These AML liposomes did show a lower affinity for liver and spleen (Column 4 of FIG. 2) and a slightly increased uptake by tumor compared to that provided by AM/2 liposomes (Column 2 of FIG. 2). However, this level of tumor-associated radioactivity was still three to ten times less than observed in the experiments with neutral, positive and negative liposomes as shown in FIG. 1.

In further experiments, applicants injected mice with either a saline solution or with 8 mg AM/2 liposomes. The saline solution provided a control and did not block the macrophages in the liver and spleen in the manner discussed above. This is shown in FIG. 3. The AM/2 liposomes provided a positive charge and were effective in blocking the macrophages in the liver and spleen. This is also shown in FIG. 3. Since the macrophages in the liver and spleen were blocked, any subsequent injection of phospholipid vesicles into the blood stream of the body had an increased opportunity to become targeted to the tumor.

One hour after the injection of the liposomes as discussed in the previous paragraph, 1 mg of the type of liposomes discussed above in relation to FIG. 1 was injected in the mice. These liposomes contained In-111. Twenty-four (24) hours afterwards, mice were sacrificed and dissected to determine biodistribution of In-111.

FIG. 1 indicates the amount of In-111 targeted to the different parts of the body when phospholipid vesicles containing In-111 are introduced into the blood stream without any previous blockade of the macrophages in the liver and spleen. In contrast, FIG. 3 indicates the amount of In-111 targeted to the different parts of the body when phospholipid vesicles containing In-111 are introduced into the blood stream after a previous blockade of the macrophages in the liver and spleen. As will be seen, the amount of the In-111 targeted to the tumor significantly increased in most instances in FIG. 3 for the individual phospholipid vesicles than for the corresponding phospholipid vesicles in FIG. 1. Furthermore, the amount of the In-111 received at the liver and spleen in FIG. 3 is significantly reduced from the amount of the In-111 received at the liver and spleen in FIG. 1.

As will be seen from a comparison of FIGS. 1 and 3, a significant amount of the phospholipid vesicles is targeted to the tumor even when the macrophages in the liver and spleen are not previously blocked. However, the amount of phospholipid vesicles targeted to the tumor is substantially increased when the macrophages in the liver and spleen are blocked before the phospholipid vesicles to be targeted to the tumor are introduced into the body.

In the experiments discussed above, the phospholipid vesicles to be targeted to the tumor were introduced into the blood stream approximately one (1) hour after the introduction of the phospholipid vesicles into the bloodstream to block the macrophages in the liver and spleen. It will be appreciated, however, that other time periods may also be used, including time periods considerably shorter than one (1) hour. Since the phospholipid vesicles blocking the liver and spleen are effective for an extended period, the introduction of the phospholipid vesicles to target the tumor may be considered as concurrent with the introduction of the phospholipid vesicles to block the liver and spleen.

As previously described, neutral DSPC:Ch phospholipid vesicles deliver In-111 to EMT6 murine tumors in sufficient quantity to allow definitive localization of tumor by gamma camera imaging. This tumor-associated specific radioactivity (% dose/gram tissue) is equal to levels achieved in liver and spleen, a finding which was not previously observed by others employing liposomes as tumor imaging agents.

There are several improvements in liposome technology employed in the present invention which may explain why better tumor imaging is achieved than has been previously observed by others. One such improvement is that applicants have loaded In-111 into preformed liposomes. By this highly efficient method, specific activities of 200–300 $\mu$Ci In-111/ mg lipid have been obtained. Another improvement is that applicants have used highly purified phospholipid vesicles as discussed above.

A further improvement has been that In-111 has been encapsulated in the NTA complex. NTA is a relatively weak chelator and, in the presence of serum, NTA is displaced. Thus, when the phospholipid micelles containing the In-111 are targeted to the tumor, the NTA becomes displaced by protein at the tumor. The In-111 becomes tightly associated with the protein at the tumor. Since this protein is within a cell, the In-111 is fixed at the position of the tumor. This circumstance provides two distinct advantages for the purpose of imaging. The first is that little radioactivity is lost due to leakage. After correcting for decay, applicants typically observed that 90% of the initial radioactivity remained in the animal at least twenty-four (24) hours after injection, based on the times required to accumulate a fixed number of counts with gamma counter. A second advantage is that when a label such as In-111 remains fixed at the site of liposome destruction, one can obtain information on rate, as well as total amount, of liposome uptake by the tissue.

Thus, the high tumor specific activities observed in this study are the result of a continuous accumulation of In-111 within the tumor over a twenty-four (24) hour period. By comparison, EDTA contained within stearylamine vesicles forms a strong chelate in comparison to NTA. EDTA is not displaced at the tumor by proteins. Thus, the In-111 will not remain fixed within the cell. For example, when EDTA was chelated to In-111 in a phospholipid vesicle, only 25% of tumor specific activity was achieved, compared to In-111 NTA loaded liposomes.

The phospholipid vesicles may be used to provide an enhanced delivery of drugs or radionuclides to tumors in the body. This may be seen from the results of experiments specified in the table constituting FIG. 4. In these experiments [$^3$H] Methotrexate (MTX) was injected directly into tumor-bearing mice as a control. The amount of the [$^3$H] MTX is directed to the tumors after a period of four (4) hours is illustrated in the row designated in FIG. 4 as "Free [$^3$H]MTX".

Phospholipid vesicles containing DSPC:Ch:SA in the ratio of 4:1:1 were labeled with [$^{14}$C] cholesteryl oleate and the [$^3$H]MTX was entrapped in the phospholipid vesicles. As will be seen, the amount of the phospholipid vesicles targeted to the tumors is almost three (3) times greater than the amount of the free MTX directed to the tumor.

The liver and spleen were also blocked in the manner described above and shown in FIG. 2 before the phospholipid vesicles containing DSPC:Ch:SA, as described in the previous paragraph, were targeted to the tumors. The last column of the table in FIG. 4 illustrates the targeting of these phospholipid vesicles to the tumors after the blocking of the liver and spleen. As will be seen, the amount of the phospholipid vesicles targeted to the tumors under such circumstances was almost the same as the amount discussed in the previous paragraph.

As indicated previously, the micellular particles are to be less than 2000A° in diameter, preferably in the 500 to approximately 700A° range. To demonstrate further the significance of such size limitation, Table I shows biodistribution data from four mice that received REV vesicles containing In-111 NTA. The larger vesicles were prepared by reversed phase evaporation following the method of Syoka and Papahadjopoulos, *Proc. Natl. Acad. Sci. U.S.A.*, 75:4194–4198 (1978), and were approximately five times larger than SUV's, but with identical chemical composition. To maximize tumor accumulation of the radiolabel agent, the animals were sacrificed when the mean lesion size was only 4±1 mg. Such structures, approximately 2 millimeters in largest dimension, were within the limits of the dissection technique. Uptake of REV's by the malignancies was only 2.1±0.1% ID/g. This value was somewhat above blood levels, but one tenth or less than that found in comparably sized Lewis Lung Carcinomas using SUV's (Table 2). In order to establish that tumor size effects are not different for the larger vesicles, two additional mice were injected with REV's when their carcinomas were considerably larger. Tumor accumulations were 1.5 and 1.2% ID/g in 320 and 2.10 mg lesions respectively. Thus, larger vesicles of DSPC-:Chol have very significantly reduced accumulation in Lewis Lung Carcinoma (p<0.005 using Tables 1 and 2).

It has also been found that tumor uptake of encapsulated agent decreases significantly with increasing tumor size. For LLC lesions between 0.1 and 0.5 g, uptake varied between 25 and 12% ID/g. Very small metastases (4 and 8 mg) found in the lung after s.c. implantation had uptake of approximately 50% ID/g. For larger lesions, a slow decrease in tumor accumulation was observed out to 1.8 g where the value approached some 10% ID/g. Most of the variation with size occurred in the range 0.02 to 0.2 g; i.e. between 0.1 and 1.0% of the animal's total mass. It was observed during dissection that the larger tumors had relatively enhanced necrotic zones, which explains, at least in part, this dependence upon size.

Although this invention has been described and illustrated with reference to particular applications, the principles involved are susceptible of numerous other applications which will be apparent to persons skilled in the art. The invention is, therefore, to be limited only as indicated by the scope of the appended claims.

TABLE 1

BIODISTRIBUTION OF REVERSED PHASE
EVAPORATION VESICLES (REV) IN MICE WITH
LEWIS LUNG CARCINOMA AND GRANULOMA

| Tissue | % injected dose per per gram of tissue* |
|---|---|
| Blood | 1.1 ± 0.2 |
| Tibias | 5.5 ± 0.5 |
| Lung | 3.7 ± 0.8 |
| Liver | 50.7 ± 2.1 |
| S & L Intestine# | 0.9 ± 0.0 |
| Kidney | 5.9 ± 0.3 |
| Spleen | 73.2 ± 13.9 |
| Carcass | 0.9 ± 0.1 |
| Stomach# | 0.2 ± 0.0 |
| Muscle | 0.3 ± 0.0 |

TABLE 1-continued

BIODISTRIBUTION OF REVERSED PHASE
EVAPORATION VESICLES (REV) IN MICE WITH
LEWIS LUNG CARCINOMA AND GRANULOMA

| Tissue | % injected dose per per gram of tissue* |
|---|---|
| Skin | 0.8 ± 0.0 |
| S.C. LLC Tumor | 2.1 ± 0.1 |
| Granuloma | 0.6 ± 0.1 |
| % of Recovery | 81.8 ± 0.9 |
| Tumor Mass (mg) | 4 ± 1 |

*Mean values ± standard error of the mean
N = number of mice per group
values include organ contents

TABLE 2

TISSUE DISTRIBUTION OF VESICLE-ENCAPSULATED
IN-111-NTA IN MICE WITH SUBCUTANEOUSLY
IMPLANTED LEWIS LUNG CARCINOMA

| | 24 h % Injected Dose Per Gram of Tissue* Number of days after subcutaneous implantation of Lewis Lung Carcinoma | | |
|---|---|---|---|
| Tissue | 8<br>N = 4+ | 11<br>N = 4+ | 17<br>N = 4+ |
| Blood | 8.1 ± 0.1 | 11.4 ± 2.3 | 1.3 ± 0.4 |
| Tibias | 6.4 ± 0.6 | 6.8 ± 0.6 | 4.7 ± 0.7 |
| Lung | 5.7 ± 0.5 | 15.1 ± 1.4 | 12.6 ± 1.6 |
| Liver | 50.0 ± 2.4 | 50.5 ± 1.9 | 36.1 ± 3.2 |
| S & L Intestine# | 4.3 ± 0.2 | 4.9 ± 0.6 | 1.8 ± 0.3 |
| Kidney | 15.1 ± 0.5 | 15.8 ± 0.4 | 9.2 ± 0.2 |
| Spleen | 57.0 ± 5.6 | 50.0 ± 6.7 | 22.2 ± 3.2 |
| Carcass | 2.3 ± 0.1 | 2.8 ± 0.2 | 1.6 ± 0.1 |
| Stomach* | 3.5 ± 0.6 | 4.3 ± 1.3 | 1.5 ± 0.5 |
| Muscle | 1.1 ± 0.1 | 0.8 ± 0.0 | 0.4 ± 0.0 |
| Skin | 5.6 ± 2.7 | 2.1 ± 0.3 | 2.4 ± 0.2 |
| s.c. LLC Tumor | 23.7 ± 2.7 | 17.0 ± 3.3 | 9.8 ± 0.9 |
| % Recovery | 102.8 ± 0.6 | 105.0 ± 1.9 | 91.3 ± 1.5 |
| Tumor mass (g) | 0.13 ± 0.04 | 0.16 ± 0.04 | 1.67 ± 0.39 |

*Mean values ± standard error of the mean
+ N = number of mice per group
Values include organ contents

What is claimed is:

1. A method of targeting a tumor in a body with an agent for diagnosis or treatment, comprising:
   a) providing micellular particles of less than 2000 Å comprising phospholipid molecules wherein said particles are stable to leakage in vitro and in vivo, and
   b) modifying a portion of said phospholipid micellular particles to provide for the blockage of the macrophages in the body by such modified phospholipid micellular particles;
   c) initially introducing the modified vesicles into the blood stream of the body to block uptake by the macrophages in the body;
   d) incorporating said agent for diagnosis or treatment into a second group of the micellular particles; and
   e) subsequently introducing the second group of phospholipid micellular particles with said agent for diagnosis or treatment into the blood stream of the body to obtain movement of the particles to the tumor.

* * * * *